US009878964B2

United States Patent
Rothaemel et al.

(10) Patent No.: US 9,878,964 B2
(45) Date of Patent: Jan. 30, 2018

(54) PROCESS AND PLANT FOR PRODUCING OLEFINS FROM OXYGENATES

(71) Applicant: L'Air Liquide, Societe Anonyme pour l'Etude et l'Exploitation des Procedes Georges Claude, Paris (FR)

(72) Inventors: Martin Rothaemel, Frankfurt am Main (DE); Roberta Olindo, Frankfurt am Main (DE); Stephane Haag, Frankfurt (DE); Thomas Renner, Frankfurt am Main (DE); Frank Castillo-Welter, Friedrichsdorf (DE)

(73) Assignee: L'AIR LIQUIDE SOCIÉTÉ ANONYME POUR L'ÉTUDE ET L'EXPLOITATION DES PROCEDES GEORGES CLAUDE, Paris (FR)

( * ) Notice: Subject to any disclaimer, the term of this patent is extended or adjusted under 35 U.S.C. 154(b) by 164 days.

(21) Appl. No.: 14/768,582

(22) PCT Filed: Feb. 4, 2014

(86) PCT No.: PCT/EP2014/052165
§ 371 (c)(1),
(2) Date: Aug. 18, 2015

(87) PCT Pub. No.: WO2014/124845
PCT Pub. Date: Aug. 21, 2014

(65) Prior Publication Data
US 2015/0376080 A1 Dec. 31, 2015

(30) Foreign Application Priority Data
Feb. 18, 2013 (DE) .................. 10 2013 101 578

(51) Int. Cl.
*C07C 1/20* (2006.01)
*C07C 5/10* (2006.01)
(Continued)

(52) U.S. Cl.
CPC .............. *C07C 1/20* (2013.01); *B01J 19/245* (2013.01); *C07C 5/10* (2013.01); *C07C 6/04* (2013.01);
(Continued)

(58) Field of Classification Search
CPC .... C07C 1/20; C07C 5/10; C07C 6/04; C07C 2529/18; C07C 2529/40; B01J 19/245;
(Continued)

(56) References Cited

U.S. PATENT DOCUMENTS

| 4,482,772 A | 11/1984 | Tabak |
| 4,543,435 A | 9/1985 | Gould et al. |

(Continued)

FOREIGN PATENT DOCUMENTS

| DE | 102005048931 | 4/2007 |
| WO | WO 2006 136433 | 12/2006 |
| WO | WO 2011 131 647 | 10/2011 |

OTHER PUBLICATIONS

International Search Report for PCT/EP2014/052165 dated Apr. 9, 2014.

*Primary Examiner* — Brian McCaig
*Assistant Examiner* — Jason Chong
(74) *Attorney, Agent, or Firm* — Justin K. Murray

(57) ABSTRACT

A process for producing olefins from oxygenates comprises the following steps:
(i) heterogeneously catalyzed conversion of at least one oxygenate to an entire stream containing propylene, aromatics and cyclic olefins;
(ii) olefin interconversion of at least a part of the entire stream;

(Continued)

(iii) separation of a stream rich in aromatics from the reaction product of the olefin interconversion; and
(iv) hydrogenation of the stream rich in aromatics.

8 Claims, 3 Drawing Sheets

(51) Int. Cl.
*C07C 6/04* (2006.01)
*C10G 45/44* (2006.01)
*C10G 69/04* (2006.01)
*C10G 3/00* (2006.01)
*C10G 11/02* (2006.01)
*B01J 19/24* (2006.01)

(52) U.S. Cl.
CPC ............... *C10G 3/42* (2013.01); *C10G 11/02* (2013.01); *C10G 45/44* (2013.01); *C10G 69/04* (2013.01); *B01J 2219/24* (2013.01); *C07C 2529/18* (2013.01); *C07C 2529/40* (2013.01)

(58) Field of Classification Search
CPC ...... B01J 2219/24; C10G 69/04; C10G 11/02; C10G 45/44; C10G 3/42
See application file for complete search history.

(56) References Cited

U.S. PATENT DOCUMENTS

| | | | |
|---|---|---|---|
| 5,773,670 A * | 6/1998 | Gildert | B01D 3/009 203/DIG. 6 |
| 2006/0161035 A1 | 7/2006 | Kalnes et al. | |
| 2007/0284284 A1 | 12/2007 | Zones et al. | |
| 2009/0124841 A1* | 5/2009 | Rothaemel | B01D 3/143 585/639 |
| 2011/0319686 A1* | 12/2011 | Rothaemel | C07C 1/20 585/312 |

* cited by examiner

US 9,878,964 B2

PROCESS AND PLANT FOR PRODUCING OLEFINS FROM OXYGENATES

CROSS REFERENCE TO RELATED APPLICATIONS

This application is a §371 of International PCT Application PCT/EP2014/052165, filed Feb. 4, 2014, which claims the benefit of DE 10 2013 101 578.6, filed Feb. 18, 2013, both of which are herein incorporated by reference in their entireties.

TECHNICAL FIELD OF THE INVENTION

The present invention relates to a process for producing olefins from oxygenates, with the following steps: (i) heterogeneously catalyzed conversion of at least one oxygenate to a stream containing propylene, aromatics and cyclic olefins, and (ii) olefin interconversion of at least one partial stream of the stream containing propylene, aromatics and cyclic olefins. Furthermore, the invention comprises a plant for carrying out this process.

BACKGROUND

Propene ($C_3H_6$), often also referred to as propylene, is one of the most important starting substances of the chemical industry. The demand for the base material propylene is increasing worldwide, wherein propylene just like ethylene mostly is produced from petroleum in a steam cracker in a ratio dependent on the process conditions and the raw materials.

To obtain additional propylene, a number of processes exist, such as the PDH process which proceeds from propane as educt. What is known, however, above all is the so-called MTP process, in which olefins are produced from methanol (MeOH) or dimethyl ether (DME) by catalytic conversion on a zeolitic catalyst. By varying the catalyst and the process conditions, the selectivity of the products obtained can be influenced and the product spectrum thus can be shifted towards short-chain olefins (then often also the process name Methanol-to-Olefin (MTO)), towards longer-chain products (then often also the process name Methanol-to-Gasoline (MTG)) or towards propylene.

The fundamentals of an MTP process are described for example in DE 10 2005 048 931 A1. From an educt mixture containing steam and oxygenates such as methanol and/or dimethyl ether, $C_2$ to $C_4$ olefins are produced above all. By a heterogeneously catalyzed reaction in at least one reactor, the educt mixture is converted to a reaction mixture comprising low-molecular olefins and gasoline hydrocarbons. By a suitable separation concept, higher olefins, above all the $C_{4+}$ fraction, can at least partly be recirculated into the reactor as recycling stream and in said reactor for the most part be converted to propylene, whereby the yield of propylene is increased.

The MTP process usually has a propylene yield of about 65% (mole C). An increased yield would distinctly improve the economy of the process. As predominant by-product in the MTP process a gasoline-like mixture (MTP gasoline) is obtained, which substantially consists of olefins, paraffins, cycloparaffins, cycloolefins and aromatics. This MTP gasoline likewise can be incorporated into a succeeding value chain, but has a lower market price than propylene.

As described in WO 2006/136433 A1 it therefore partly is attempted to subject the MTP gasoline to a post-processing in the form of an olefin interconversion, in which the MTP gasoline is converted on a zeolitic catalyst at temperatures of about 400 to 500° C. and a pressure of 1 to 5 bar. Due to this downstream reaction, a moderate increase of the propylene yield of the entire process can be achieved, but the total yield still lies below 70% (mole C).

A direct recirculation of the MTP gasoline into the MTP reactor provides no increase in the yield of propylene. Since undesired alkylation reactions of the aromatics occur inside the MTP reactor, which consume methanol which then no longer is available for the selective formation of propylene, the propylene yield of the entire process even would decrease.

Some processes therefore aim at converting the heavier olefins obtained, so that at least a product with homogeneous composition and higher market price is obtained. U.S. Pat. No. 4,543,435 for example teaches that at least a part of the olefins obtained is to be converted to heavy hydrocarbons, so that the yield of liquefied gas and gasoline can be increased within the MTO process.

WO 2011/131647 describes a process for producing aromatic hydrocarbons, in which a feed of light alkanes is at least partly converted to aromatics on a suitable catalyst. Parallel thereto an MTO process takes place. A part of the oxygenate feed of the MTO process is produced in that the hydrogen obtained during the conversion of the alkanes to aromatics is converted to an oxygenate with carbon monoxide and/or carbon dioxide. The product streams thus obtained can easily be combined with the other by-products of the MTO process, above all methane, carbon oxides, hydrogen and a product similar to liquefied gas.

For increasing the yield of valuable products from an MTO process, a hydrogenation of the aromatic hydrocarbons obtained also is known. US 2004/0039239 for example teaches that higher olefins are to be hydrogenated on a suitable hydrogenation catalyst. In particular due to the fact that aromatics also are hydrogenated to paraffins, the yield of a gasoline-like valuable product thus can be increased.

From U.S. Pat. No. 4,482,772 a hydrogenation within an MTO process is known, in which first the conversion of the oxygenates to olefins takes place and the olefins thus obtained subsequently are oligomerized. Subsequent to the oligomerization, at least parts of the product stream are hydrogenated, whereby aromatics contained in the product stream are converted to naphthenes. The yield of a gasoline-like valuable product likewise can further be increased thereby.

For carrying out such hydrogenations, various types of catalyst and their possible applications are known for example from US 2007/0284284 A1.

However, since all by-products of the MTP process thus obtained have a lower market value than the actual target product propylene, it can only partly be compensated with this process that the propylene yield maximally is about 65%.

SUMMARY OF THE INVENTION

Therefore, it is the object of the present invention to provide a process in which proceeding from oxygenates the propylene yield can distinctly be increased.

This object is solved by a process with the features of the claims.

In a first process step (step (i)) of an embodiment of the invention, at least one oxygenate is heterogeneously catalytically converted to a stream containing propylene, aromatics and cyclic olefins. Preferably, the oxygenate feed at least partly consists of methanol, preferably it consists of methanol for more than 99 vol-%. However, the use of crude methanol (max. 30% water), pure DME or DME/methanol mixtures also is possible. Subsequently, at least parts of the olefins and aromatics obtained are subjected to an olefin interconversion (OI) (step (ii)), so as to obtain an interconverted stream. From the interconverted stream aromatics and cyclic olefins are at least partly separated (step (iii)). Finally, at least one partial stream of the interconverted stream is hydrogenated (step (iv)). This stepwise conversion has the advantage that individual streams are selectively separated, in order to supply them to a further conversion in which they can optimally react further to obtain propylene. In the olefin interconversion, olefins contained in the conventional MTP gasoline thus are largely converted to ethylene and propylene. These and other light components then can easily be separated from the interconversion product. Due to the separation after the interconversion it is possible to recirculate the short-chain olefins obtained, above all the $C_2$ and $C_3$ fractions, into the processing of the process.

The olefin interconversion utilizes an acidic molecular sieve as catalyst, wherein in particular zeolites, quite preferably a zeolite of the type ZSM-5, are employed. Suitable reaction temperatures are temperatures in the range from 200 to 600° C., preferably 350 to 550° C., particularly preferably 400 to 520° C. The reaction takes place at pressures between 0.5 and 5 bar, wherein an almost complete conversion (turnover >95%) based on the $C_{5+}$ olefins occurs. Since the conversion of the longer-chain olefins is endothermal and takes place by adding volume, the addition of an inert diluent is advantageous, which thus decreases the adiabatic temperature decrease in the reactor and increases the mean reactor temperature, so that the reactions proceed faster and with a higher turnover. At the same time, the partial pressures of the reacting components are lowered by adding an inert diluent, which due to the increase in volume of the splitting reaction likewise leads to a larger turnover. It is preferred particularly when the inert diluent consists of 1-100 mol-% of hydrogen, since the same can easily be separated by condensation after passage through the reactor. Furthermore, the inert diluent also can contain nitrogen, methane or other suitable gases.

In a particularly advantageous configuration of the olefin interconversion the reaction product is cooled, wherein three phases are formed: (1) a light fraction containing $C_{4-}$ hydrocarbons with the propylene obtained can directly be recirculated into the existing processing of the MTP core process; (2) the aqueous phase can directly be recirculated into the olefin interconversion; and (3) a liquid residual product rich in aromatics, which is at least partly supplied to the hydrogenation.

Due to the hydrogenation reactions taking place, aromatics and cyclic olefins are converted to cycloparaffins. In that in the olefin interconversion process the olefins contained largely react to ethylene and propylene and subsequently can be separated, the residual stream rich in aromatics exclusively is hydrogenated, which is why the hydrogenation can be designed correspondingly small.

For the hydrogenation reaction, hydrogen ($H_2$) advantageously is used as hydrogenating agent. Since the aromatics and cyclic olefins originate from the MTP reaction, they include no inorganic catalyst poisons such as sulfur etc. Thus, very moderate conditions at temperatures of less than 150° C. and pressures of less than 25 bar can be used for the hydrogenation, in order to achieve an almost complete conversion. There can be used standard hydrogenation catalysts, which contain e.g. nickel or palladium as active component which is applied on a carrier, e.g. activated carbon.

Moreover, it was found to be advantageous to carry out the hydrogenation such that the ratio between hydrogenated product and non-hydrogenated feed stream, which contains aromatics and cyclic olefins, lies between 0.1:1 and 20:1 (by weight). By setting this ratio, a dilution of the educts to be converted can be achieved. This is necessary because the hydrogenation is a strongly exothermal reaction and otherwise too strong heating of the reaction mixture occurs within the hydrogenation, which might lead to undesired decomposition reactions or a deactivation of the hydrogenation catalysts used. The use of hydrogenated product as diluent has the advantage that no further components are introduced into the process. In the hydrogenated product a distinction must be made between liquid product streams and gaseous product streams, which substantially consist of non-converted hydrogen and formed light gases. Due to the greater density it is advantageous to use the liquid product for diluting the hydrogenation.

The molar excess of hydrogen should lie between 100 and 5000% of the quantity theoretically necessary for the complete saturation of all existing double and aromatic bonds. Thus, a limitation of the reaction due to local hydrogen concentrations can completely be excluded. Similar to the recycle of hydrogenated liquid product, the excess of hydrogen also serves the limitation of the increase in temperature of the exothermal hydrogenation reaction.

By separating hydrogen after the hydrogenation, this excess of hydrogen is irrelevant for the further processing of the hydrogenated stream, and the non-converted hydrogen also can be recirculated into the hydrogenation, so that actually no increased hydrogen consumption occurs. Correspondingly, only the stoichiometrically necessary quantity of hydrogen must be added continuously. An enrichment of gaseous by-products of the hydrogenation, such as e.g. methane, can be controlled in that a continuous small purge stream is removed from the process part.

In a particularly preferred configuration of the entire process, the oxygenate conversion reaction is effected in two stages, wherein in the first stage the at least one oxygenate first is/are converted to at least one corresponding ether and in the second stage the ether(s) is/are converted to olefins. When methanol is used as oxygenate, a conversion of the methanol to dimethyl ether first is effected and subsequently the conversion of the dimethyl ether to propylene and other olefins, in particular also to aromatics and cyclic olefins. In this two-stage configuration it is recommendable to recirculate the oxygenate, preferably the methanol, already to before the first stage, i.e. before the conversion to dimethyl ether, while the vaporous water is introduced between the first and the second stage, as it must first be used as educt for the conversion of the ether to olefins. Thus, in the first stage no unnecessary water is used, which negatively influences the equilibrium reaction during the etherification; the steam however is available as diluent for the olefin formation.

The product from the oxygenate conversion reaction initially is cooled by means of methods known to the skilled person, wherein water and water-soluble components such as oxygenates (methanol, DME) are condensed out and thus can easily be separated from the remaining hydrocarbon product. The resulting aqueous stream then is supplied to a suitable separating means (e.g. a distillation column), wherein the oxygenates are recirculated into the first reaction stage, as described above. The amount of water resulting from the conversion of the oxygenates is removed from the process, while the residual amount is recirculated to before the second reaction stage, as described above, so that closed circuits are obtained for the most part.

The largely water-free hydrocarbon stream is compressed after the cooling; there is obtained a pressurized light hydrocarbon stream and a liquid, likewise pressurized heavy hydrocarbon stream. To safely separate possibly still contained lighter olefins, it is recommendable to switch a further separation stage in which possibly still contained $C_{4-}$ fractions can be removed from the $C_{5+}$ fraction. Advantageously, this separation stage is a distillation, in order to ensure a sufficient separation sharpness. In accordance with a development of the invention it is also recommendable to separate the $C_{6-}$ fraction from the $C_{7+}$ fraction after the heterogeneously catalyzed conversion (step (i)). While the $C_{6-}$ fraction can again directly be supplied to the oxygenate conversion reaction, the $C_{7+}$ fraction can be passed into the olefin interconversion.

After passage through the olefin interconversion, a partial stream of the product, which contains $C_{4-}$ components, can be recirculated into the separating system after the oxygenate conversion, preferably into a processing stage for short-chain olefins, wherein a recirculation into the column for separating the $C_{4-}$ fraction from the $C_{5+}$ fraction was found to be particularly useful. It can thereby be ensured that the quality of the end product remains the same and no propylene obtained gets lost.

The liquid residual product rich in aromatics, which is left after the olefin interconversion, then is passed into the hydrogenation (step (iv)), where a conversion of cyclic olefins and aromatics to cyclic paraffins is effected. It was found to be advantageous when after the hydrogenation (step (iv)) at least parts of the hydrogenated product are separated and recirculated into the olefin interconversion (step (ii)). As a result, olefins with shorter chain length and thus higher market price can be produced from the hydrogenated products.

Embodiments of the present invention may furthermore comprise a plant with the features of claim 26. Such plant is particularly useful for carrying out a process according to any of the process claims and includes a reactor for the heterogeneously catalyzed conversion of an oxygenate to a stream containing propylene, aromatics and cyclic olefins, a reactor for the interconversion of at least a part of the olefins, a separating means for separating at least a part of the aromatics from the product stream of the interconversion, and a reactor for hydrogenating at least parts of the aromatics. With this plant it can be achieved that aromatics and double-bond systems are hydrogenated and the longer-chain and cyclic paraffins thus obtained can be processed such that short-chain olefins are obtained, in particular also the valuable product propylene. Other olefin fractions, however, are subjected to an interconversion and separated already before the hydrogenation, which is why the hydrogenation can be dimensioned very small. A further advantage of this plant design consists in that already existing plants can be retrofitted with reactors for the olefin interconversion and for the hydrogenation of the aromatics and cyclic olefins and with the separating means, so that the propylene yield also can be increased in existing plants.

Further developments, advantages and possible applications of the invention can also be taken from the following description of an exemplary embodiment and the drawing. All features described and/or illustrated form the subject-matter of the invention per se or in any combination, independent of their inclusion in the claims or their back-reference.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

Figure 1:
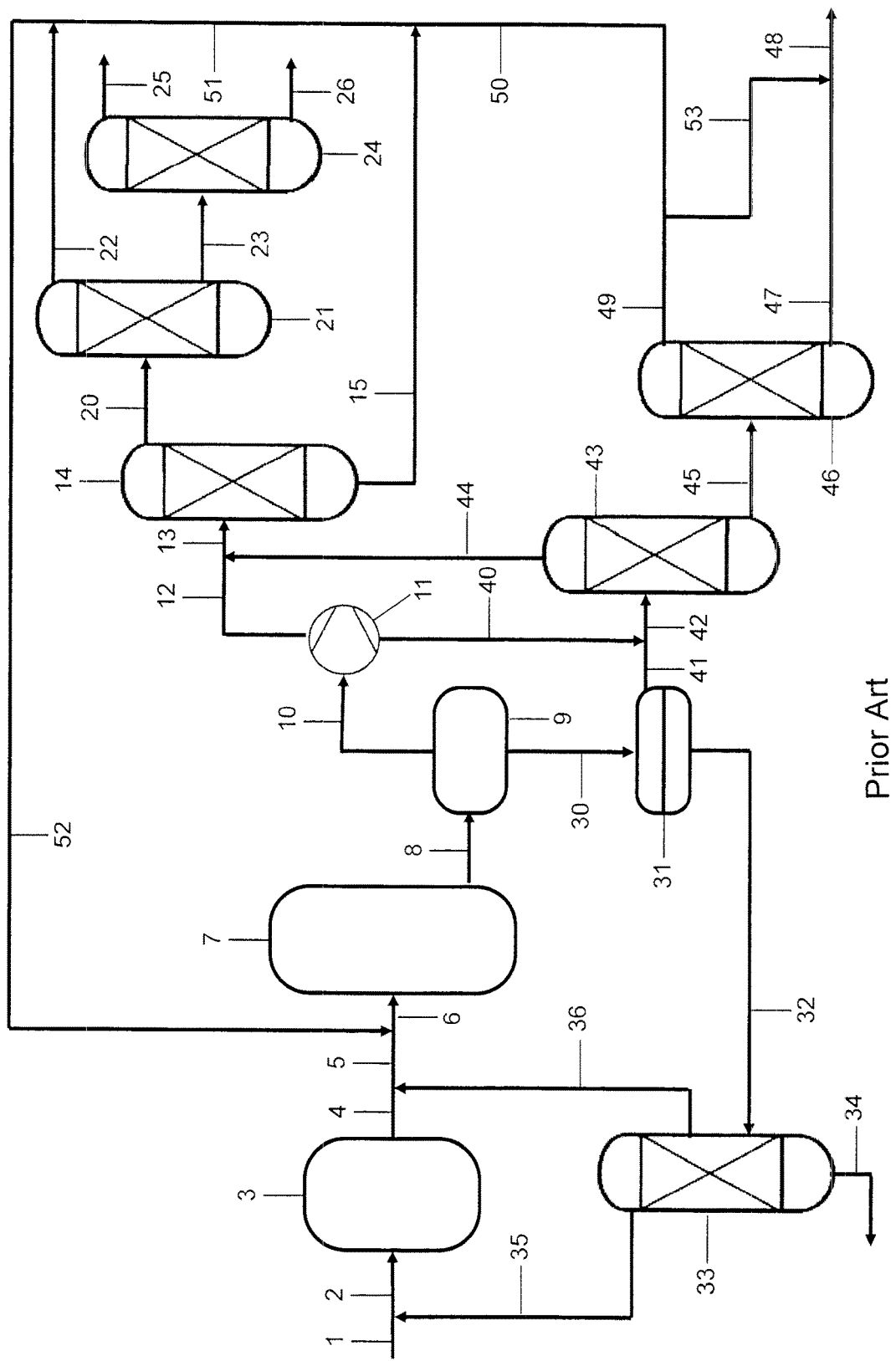
FIG. 1 schematically shows a usual MTP process.

FIG. 1 shows the MTP production according to the prior art. Via conduits 1 and 2, methanol is introduced into a reactor 3 in which the methanol is at least partly converted to dimethyl ether. Via conduits 4, 5 and 6, the dimethyl ether is withdrawn and supplied to a second reactor 7 in which the dimethyl ether together with steam is converted to olefins. The olefin stream thus obtained contains propylene and other olefins, but also cyclic olefins and aromatics.

Via conduit 8, the product stream obtained is introduced into the cooling device 9. There, a gaseous phase separates from a liquid phase. The gaseous phase contains the $C_{5-}$ fraction and is supplied to a compressor 11 via conduit 10. The gaseous fraction obtained in the compressor 11 is supplied to a distillation column 14 via the conduits 12 and 13. In this distillation column 14, the $C_{3-}$ fraction is separated from the $C_{4-}$ fraction.

Via conduit 20, the $C_{3-}$ fraction is supplied to a column 21 in which the $C_{2-}$ fraction is withdrawn over the head. Via conduit 22 and conduit 52, the $C_{2-}$ fraction gets back into conduit 5 and from there can be guided via conduit 6 into the reactor 7, so that here the desired product propylene is at least partly produced by olefin interconversion. To avoid an enrichment of inert light gaseous components such as methane or $CO_x$ in the circuit, a small partial quantity of the stream from conduit 22 can be removed from the system as purge via a non-illustrated conduit. Furthermore, the $C_3$ fraction is withdrawn from the column 21 via conduit 23 and supplied to a column 24. In this column 24, the desired target product propylene is distilled off over the head and withdrawn via conduit 25, while in the bottom further compounds with three carbon atoms are left and are withdrawn via conduit 26.

Via conduit 15, the bottom product of the column 14 is withdrawn from the column 14 as $C_4$ fraction, and via the conduits 51 and 52 it is likewise recirculated to before the conversion of the ether to olefins in conduit 5, in order to further increase the yield of propylene by olefin interconversion. To avoid an enrichment of butane (a component inert for the conversion in the reactor) in the circuit, a small partial quantity of the stream from conduit 15 can be removed from the system as purge via a non-illustrated conduit.

The liquid fraction obtained in the cooler 9 is supplied to a separator 31 via conduit 30. The aqueous phase separated in the separator 31 also contains oxygenates (when using methanol as educt, above all methanol) and is supplied to a column 33 via conduit 32.

From the column 33 water is discharged from the bottom via conduit 34. Furthermore, steam is withdrawn from the column 33 via conduit 36 and fed into conduit 4, from where the steam gets into the reactor 7 via conduit 5 and conduit 6, in which reactor it is used as diluent for the conversion of the oxygenates to olefins.

The top product of the column 33, at least one oxygenate, preferably methanol, is fed into the conduit 1 via conduit 35 and thus gets into the reactor 3 via conduit 2. When methanol is used as educt, recovered methanol together with the methanol fed in as educt thus is converted to dimethyl ether. Alternatively, the oxygenate also can directly be recirculated into the reactor 7 together with the steam via conduit 36.

The organic phase withdrawn from the separator contains the $C_{5+}$ fraction, which is discharged via conduit 41 and passed on via a pump (not shown). To this $C_{5+}$ fraction, the liquid fraction obtained from the compressor 11 at 15-25 bar then is also admixed via conduit 40. The combined streams then are introduced into a column 43 via conduit 42.

From the head of the column 43, the $C_{4-}$ fraction is introduced via conduit 44 into the conduit 12, from where it is fed into the column 14 together with the gaseous part from the compressor 11 via conduit 13.

Via conduit 45, the bottom product of the column 43, which contains the $C_{5+}$ fraction, is guided into the column 46. From the bottom of the column 46, the $C_{7+}$ fraction is withdrawn into the conduits 47 and 48.

Over the head of the column 46, the $C_5/C_6$ fraction obtained is recycled via the conduits 49, 50, 51 and 52, in that it is recirculated into the conduit 5. Parts of the $C_5$ and $C_6$ fraction are supplied to the conduit 47 via conduit 53 and discharged from the process via conduit 48 (purge). The stream leaving the process via conduit 48 represents the MTP gasoline.

Figure 2:
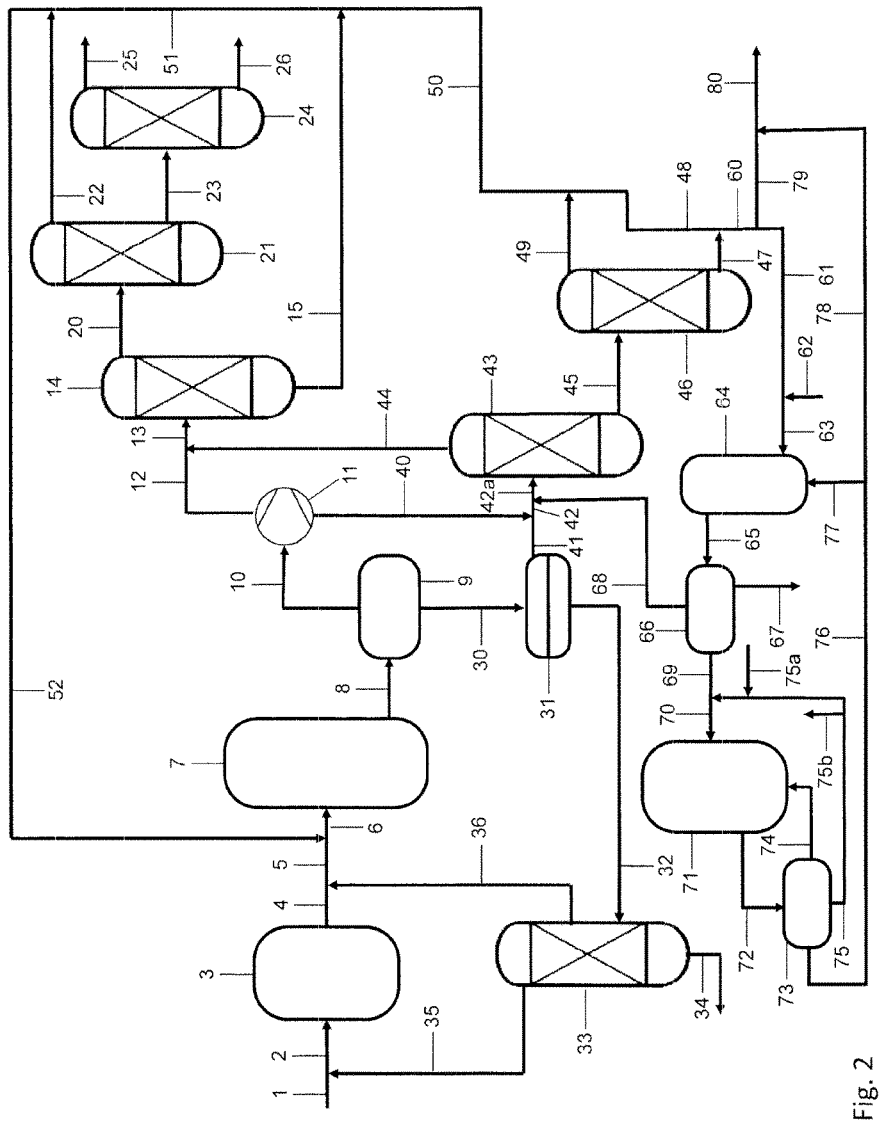
FIG. 2 schematically shows the process according to an embodiment of the invention.

FIG. 2 schematically shows the procedure of the process according to the invention. Up to the plant component 47, the plant is identical with the MTP process known from the prior art. The $C_5/C_6$ fraction, which has been obtained at the top of column 46, furthermore is recirculated into the oxygenate conversion (step (i)) by means of conduit 49, but the small waste stream, also called purge stream (conduit 48), which is necessary for limiting the enrichment of inert components in the circuit, now is admixed to the $C_{7+}$ stream (47). The mixed stream 60 is at least partly discharged from the process via conduits 79 and 80, in order to still be able to control the amount of inert components in the recycle. A large part of the stream, preferably more than 90 wt-%, particularly preferably more than 95 wt-%, is guided into the olefin interconversion 64 via conduits 61 and 63, wherein steam first has been admixed to this stream via conduit 62. Depending on the temperature of the column 46 it can be necessary to heat up the streams 62 and 63 to the reaction temperature in the reactor 64 by means of methods known to the skilled person.

After the olefin interconversion 64, the product obtained is cooled in the cooler 66 via conduit 65. As technical realization of this cooling 66 a quenching tower is recommendable. As a result of this cooling 66 a gas phase is obtained, which substantially consists of $C_{4-}$ hydrocarbons, a liquid hydrocarbon stream which contains the heavy residual components of the olefin interconversion (the $C_{5+}$ fraction), substantially aromatics and cyclic olefins, and a stream consisting of condensed steam, which possibly also contains traces of soluble organic compounds. Via conduit 67, this aqueous stream is discharged and, in a preferred configuration, can again be recirculated into the reactor 64 via conduit 62. In this case, it can be necessary to discharge a small amount, preferably less than 10%, particularly preferably less than 2%, of the stream 67 and to correspondingly add the same amount of fresh water (not shown) and then again supply the same to the system via the stream 62. Furthermore, the stream 67 can at least partly be used internally, e.g. for steam generation, or can be supplied to a water treatment.

The gas phase is guided into conduit 42 via conduit 68, whereby this stream can be subjected to the basically existing treatment via conduit 42a, and the valuable products contained therein, above all the propylene, correspondingly can be supplied to the entire propylene stream.

Via conduits 69 and 70, the liquid hydrocarbon stream is discharged from the cooler 66. It is heated to temperatures of 20 to 250° C. and at a pressure of 2 to 45 bar mixed with hydrogen from conduit 75. This entire stream is supplied to the hydrogenation reactor 71, which can be constructed as a simple fixed-bed reactor, but just as well can also be equipped with an internal cooling of the single- or multi-stage type. Catalysts useful in the hydrogenation include noble metals such as nickel, palladium and platinum or mixtures thereof on carrier materials, activated carbon, silica or alumina or mixtures thereof.

After passing the reactor 71, olefins have been hydrogenated to paraffins and the aromatics as well as cyclic olefins to cyclohexane derivatives and other cyclic paraffins. Since the hydrogenation is very exothermal, this kind of reaction preferably is designed such that it takes place in strongly diluted form. For this purpose, the reaction mixture obtained is introduced into a cooler 73 via conduit 72, in which cooler a phase separation between a gas phase rich in hydrogen and a liquid product phase takes place. From the cooler 73, the gas phase rich in hydrogen is discharged via conduit 75, mixed with the stoichiometrically necessary quantity of fresh hydrogen (conduit 75a) and again supplied to the hydrogenation reactor. Since the gas phase also can contain formed light gases such as methane, a partial stream must again be removed from the circuit at this point via conduit 75b (purge).

The liquid phase from the cooler 73 is partly recirculated into the reactor 71 via conduit 74. Due to the recirculation of hydrogenated liquid product and gas rich in hydrogen, a quantity ratio of 0.1 to 20 tons of hydrogenated liquid product per ton of non-hydrogenated feed and a molar hydrogen quantity which is 1-50 times as large as required for the complete saturation of all double and aromatic bonds is obtained in the hydrogenation 71.

Via conduits 76 and 77, the main part of the obtained hydrogenated product from the cooler 73 subsequently is recirculated into the olefin interconversion reactor 64, where the naphthenes are at least partly converted to short-chain olefins. Via conduit 65 and the cooler 66, they finally get from there into conduit 68 and thus into the processing of the short-chain olefins. The paraffins obtained from the hydrogenated olefins are inert and serve the dilution of the reaction mixture, whereby the amount of steam to be added for the interconversion is reduced. This possible reduction of the steam addition has the additional advantage to prolong the useful life of the catalyst, since its irreversible deactivation by dealuminization at the lower steam partial pressure thus obtained is slowed down.

A small part of the reaction product of the hydrogenation is supplied to the entire waste stream 80 via conduit 78, in order to control the concentration of inert components in the recycle.

As a result of the process according to the invention, the amount of the MTP gasoline obtained is distinctly reduced and there is obtained a smaller amount of a paraffin- and naphthene-containing naphtha instead of the MTP gasoline. The propylene yield of the process, however, can distinctly be increased.

The described variant has the advantage that in essence no internal streams of the MTP process are changed. What rises merely is the quantity of the $C_{5-}$ stream which is supplied to the processing. As a result, the complete core system of the MTP processing, as it is known from FIG. 1, can remain the same and need not be designed newly in terms of engineering.

Figure 3:
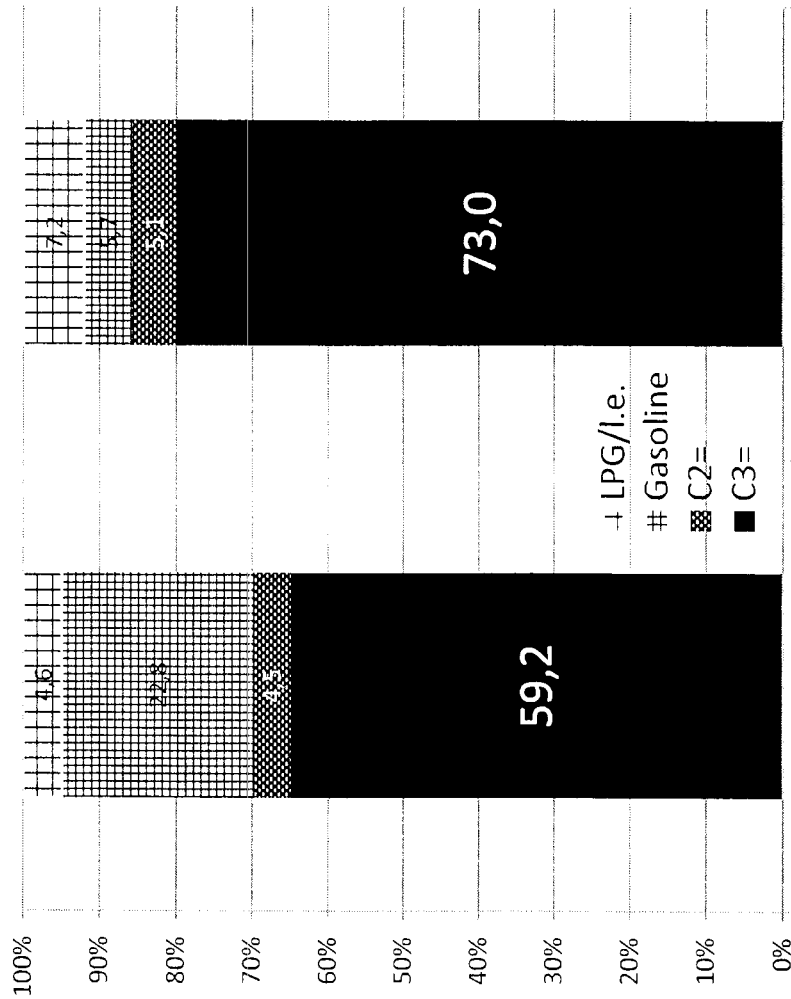
FIG. 3 shows a comparison between a usual MTP process and the MTP process according to an embodiment of the invention.

The positive effect of the described process according to the invention can be estimated according to FIG. 3.

Since the amount of gasoline can be reduced by almost ¾ as shown, the amount of propylene distinctly rises at the same time. Converted into carbon yield, the propylene yield is increased from 65 to 80%.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS 1, 2 conduit
3 reactor
4-6 conduit
7 reactor
8 conduit
9 cooler
10 conduit
11 compressor
12, 13 conduit
14 separating means
15 conduit
20 conduit
21 separating means
22, 23 conduit
24 separating means
25, 26 conduit
30 conduit
31 separator
41, 42a conduit
43 separating means
44, 45 conduit
46 separating means
47-52 conduit
60-63 conduit
64 reactor
65 conduit
66 cooler
67-70 conduit
71 reactor
72 conduit
73 cooler
74-80 conduit

The invention claimed is:

1. A process for producing olefins from oxygenates, the process comprising the following steps:
   (i) converting, by heterogeneous catalysis, at least one oxygenate to a conversion stream containing propylene, aromatics, and cyclic olefins;
   (ii) separating the conversion stream into a $C_{5-}$ fraction containing propylene, a $C_{5+}$ fraction containing aromatics and cyclic olefins, and an aqueous fraction containing oxygenates;
   (iii) subjecting at least parts of the $C_{5+}$ fraction containing aromatics and cyclic olefins to olefin interconversion to produce an interconversion stream comprising aromatics and $C_{4-}$ olefins;
   (iv) separating the interconversion stream into an aromatic-rich stream and a $C_{4-}$ olefin stream;
   (v) hydrogenating the aromatic-rich stream using hydrogen as a hydrogenating agent to form a product stream comprising cycloparaffins and non-reacted hydrogen;
   (vi) separating the product stream into a cycloparaffin stream and a hydrogen stream, recycling at least a part of the cycloparaffin stream to step (iii), and recycling at least part of the hydrogen stream to step (v); and
   (vii) recycling the $C_{4-}$ olefin stream into a stream derived from the conversion stream, thereby increasing $C_{4-}$ olefins recovery as compared to a process having an absence of steps (ii)-(vii).

2. The process according to claim 1, wherein a ratio between the recycled cycloparaffin stream and the aromatic-rich stream to be hydrogenated lies between 1:10 and 20:1 and a molar ratio of hydrogen is about 1-50 based on the quantity theoretically necessary for the complete saturation of all contained double and aromatic bonds.

3. The process according to claim 1, wherein from the aqueous fraction containing oxygenates, the oxygenates and water are separated.

4. The process according to claim 3, wherein the separated oxygenates and/or the separated water are/is at least partly recirculated into step (i).

5. The process according to claim 4, wherein the heterogeneously catalyzed conversion is effected in two stages, wherein in the first stage methanol is converted into dimethyl ether and in the second stage dimethyl ether is converted to a stream containing olefins and aromatics, and wherein methanol is recirculated to before the first stage and/or water is recirculated in the form of steam to before the second stage.

6. The process according to claim 1, wherein step (ii) further comprises separating the $C_{5+}$ fraction into a $C_{5/6}$ fraction and a $C_{7+}$ fraction, and wherein the at least parts of the $C_{5+}$ fraction subjected to olefin interconversion in step (iii) comprises the $C_{7+}$ fraction.

7. The process according to claim 6, wherein a portion of the $C_{5/6}$ fraction is combined with the $C_{7+}$ fraction prior to step (iii), and a portion of the combined stream is removed as purge stream in an amount effective for reducing the enrichment of inert compounds within the process.

8. The process according to claim 1, wherein step (vii) comprises the step of supplying the $C_{4-}$ olefin stream to a separating means for processing hydrocarbons with a chain length of 5 or less C atoms.

* * * * *